(12) United States Patent
Sykes et al.

(10) Patent No.: US 8,403,997 B2
(45) Date of Patent: Mar. 26, 2013

(54) LOWER LIMB PROSTHESIS AND CONTROL UNIT

(75) Inventors: Andrew John Sykes, Camberley (GB); Mir Saeed Zahedi, London (GB); David Moser, Southampton (GB)

(73) Assignee: Blatchford Products Limited, Hampshire (GB)

(*) Notice: Subject to any disclaimer, the term of this patent is extended or adjusted under 35 U.S.C. 154(b) by 294 days.

(21) Appl. No.: 12/282,541

(22) PCT Filed: Mar. 20, 2007

(86) PCT No.: PCT/GB2007/000973
§ 371 (c)(1),
(2), (4) Date: Sep. 11, 2008

(87) PCT Pub. No.: WO2007/110585
PCT Pub. Date: Oct. 4, 2007

(65) Prior Publication Data
US 2009/0054996 A1 Feb. 26, 2009

(30) Foreign Application Priority Data
Mar. 24, 2006 (GB) .................. 0605963.8

(51) Int. Cl.
*A61F 2/74* (2006.01)
(52) U.S. Cl. .................. 623/26; 623/24; 623/43
(58) Field of Classification Search .......... 623/24, 623/39–45
See application file for complete search history.

(56) References Cited

U.S. PATENT DOCUMENTS

| | | | |
|---|---|---|---|
| 5,405,409 A | 4/1995 | Knoth | |
| 5,571,205 A | 11/1996 | James | |
| 6,610,101 B2 | 8/2003 | Herr et al. | |
| 6,719,806 B1* | 4/2004 | Zahedi et al. | 623/24 |
| 6,755,870 B1 | 6/2004 | Biedermann et al. | |
| 6,955,692 B2 | 10/2005 | Grundei | |
| 2001/0029400 A1 | 10/2001 | Deffenbaugh et al. | |
| 2002/0052663 A1 | 5/2002 | Herr et al. | |
| 2003/0120385 A1 | 6/2003 | Etienne-Cummings et al. | |
| 2004/0039454 A1 | 2/2004 | Herr et al. | |
| 2008/0114272 A1 | 5/2008 | Herr et al. | |

FOREIGN PATENT DOCUMENTS

| | | |
|---|---|---|
| DE | 195 21 464 A1 | 3/1997 |
| EP | 0 549 855 A2 | 7/1993 |
| EP | 0 628 296 | 12/1994 |
| EP | 0 628 296 A2 | 12/1994 |

(Continued)

OTHER PUBLICATIONS

U.S. Appl. No. 60/177,108, filed Jan. 20, 2000; in re: Wittig; entitled *Electronically Conrolled Prosthetic Knee*.

(Continued)

*Primary Examiner* — Bruce E Snow
(74) *Attorney, Agent, or Firm* — Alston & Bird LLP (57) ABSTRACT

A self-teaching lower limb prosthesis, for an above-knee amputee, including a dynamically adjustable joint movement control unit arranged to control operation of the joint automatically. A control unit electrically stores a target relationship between a kinetic or kinematic parameter of locomotion and walking speed. The relationship defines a number of values of the parameter associated with different walking speeds. The control unit generates monitoring signals representative of walking speed values and values of the parameter occurring at different walking speeds. An adjustment system adjusts the control unit automatically when the monitoring signals indicate deviation from the target relationship so as to bring the parameters close to that defined by the target relationship.

12 Claims, 8 Drawing Sheets

FOREIGN PATENT DOCUMENTS

| | | |
|---|---|---|
| EP | 1 255 517 A1 | 11/2002 |
| EP | 1 267 756 A1 | 1/2003 |
| EP | 1 447 062 A2 | 8/2004 |
| EP | 1 880 694 A1 | 1/2008 |
| FR | 2 677 540 A1 | 12/1992 |
| GB | 2 280 609 A1 | 2/1995 |
| GB | 2 328 160 | 2/1999 |
| GB | 2 334 891 | 9/1999 |
| GB | 2 367 753 | 4/2002 |
| WO | WO 92/22267 A1 | 12/1992 |
| WO | WO 96/41599 A1 | 12/1996 |
| WO | WO 99/44547 A1 | 9/1999 |
| WO | WO 00/38599 A1 | 7/2000 |
| WO | WO 01/54630 A1 | 8/2001 |
| WO | WO 01/72245 | 10/2001 |
| WO | WO 2007/110585 A2 | 10/2007 |

OTHER PUBLICATIONS

U.S. Appl. No. 60/192,966, filed Mar. 29, 2000; in re: Herr; entitled *Speed-Adaptive Prosthetic Knee*.

U.S. Appl. No. 60/807,505, filed Jul. 17, 2006; in re: Sykes; entitled *Lower Limb Prosthesis and Control Unit*.

International Search Report for PCT Application No. PCT/GB2007/000973; Filed Mar. 20, 2007; Date of Completion Sep. 12, 2007; Date of Mailing Sep. 19, 2007.

\* cited by examiner

Fig.5. (SPEED BOUNDARIES)

Fig.6 (OVERVIEW)

Fig. 7  (CALIBRATION)

Fig.8

(SELF TEACH MODE)

Fig. 9 (VALVE UPDATE-ACCELN)

Fig.10 (VALVE UPDATE – CONST SPEED)

LOWER LIMB PROSTHESIS AND CONTROL UNIT

This invention relates to a self-teaching lower limb prosthesis including a dynamically adjustable joint movement control unit arranged to control operation of the joint automatically.

It is known from British Patent Application No. 2280609A to provide a lower limb prosthesis with a dynamically adjusting control system for controlling the movement of a shin part of the prosthesis about a knee axis on a thigh part of the prosthesis according to the amputee's speed of locomotion. A pneumatic piston and cylinder device coupled between the thigh part and the shin part has a motor-driven valve which alters the resistance of the device to movement at the knee joint in response to command signals from an electronic control circuit deriving input signals from a transducer mounted on the control device, the repetition rate of the input signals being representative of the speed of locomotion, particularly the step period during walking.

The control circuit includes a radio receiver for receiving command signals from a remote control transmitter operated by a prosthetist, a processor for processing the command signals and the transducer signals, and a memory for storing a map of valve settings against locomotion speed ranges. The processor has a teaching mode whereby the amputee is asked to walk at a particular speed and the system is "taught" by the prosthetist inasmuch as the prosthetist causes the valve to be adjusted under remote control in real time while the amputee is walking until the best gait is obtained. The same process is performed at different walking speeds and the prosthetist selects a valve setting for each speed which, in his or her opinion, appears to produce the best walking gait. These valve settings are stored at the end of a teaching session. In a playback mode of the processor, signals corresponding to the stored valve settings are fed to the motor-driven valve automatically according to the speed at which the amputee walks.

The above system has yielded notable improvements in gait for above-knee amputees due to its adaptation of resistance to knee joint movement to different settings suiting different walking speeds rather than relying on a fixed resistance setting for all walking speeds. These improvements have been achieved without requiring excessively lengthy sessions with the prosthetist.

A self-teaching lower limb prosthesis is disclosed in International Patent Application No. WO99/44547. This includes a dynamically adjustable knee movement control unit which controls either or both of flexion and extension of the knee joint automatically in response to a sensed step-to-step variability of at least kinetic or kinematic parameter of locomotion. The sensed variability is an electrical signal value representative of the degree of variation of the parameter measured during each of a number of steps taken by the amputee, the parameter being measured during each step which is within a predetermined range of locomotion, such as a particular walking speed range. Speeds of walking or running as speed ranges may be determined by measuring the repetition rate or the average step period of a walking or running cycle, each cycle extending, for instance, from heel contact to heel contact through stance phase and swing phase.

It is an object of the present invention to provide an alternative self-teaching prosthesis.

According to a first aspect of the invention a self-teaching lower limb prosthesis for an above knee amputee includes a dynamically adjustable knee movement control unit arranged to control flexion and/or extension movements of a knee joint of the prosthesis. A control unit electrically stores a target relationship between a kinetic or kinematic parameter of locomotion and walking speed, the relationship defining a plurality of values of the parameter associated with different respective walking speeds. The control unit also includes a monitoring system which generates monitoring signals representative of walking speed values and values of the parameter occurring during use of the prosthesis at different walking speeds. An adjustment system adjusts the control unit automatically when the monitoring signals indicate deviation of the parameter from the target relationship so as to bring the parameter closer to a value defined by the target relationship for the respective walking speed.

Typically, the adjustment is made on the basis of monitoring signals from several steps, the deviation being a mean value, for instance. In the preferred embodiment of the invention, speeds of locomotion are defined by step cycle periods, and the terms "cycle period", and "walking speed" (or "speed of locomotion") are used interchangeably in this specification as related to quantities. Iterative adjustment of the control unit setting is preferred so that the monitored parameter approaches successively closer to the target parameter value using, for each adjustment, one or more parameter values measured in respect of cycle periods within a relevant walking speed region. Such a region is, preferably, one of several contiguous regions which together constitute a range of speeds or step period values likely to be encountered.

In the preferred prosthesis, the control unit includes a damper for damping flexion of the knee joint, the damping being variable by the adjustment system. In particular, the damper may be a pneumatic piston and cylinder assembly coupling upper and lower limb components which are joined together by the knee joint, the piston and cylinder assembly having a motor driven valve for varying the area of an orifice through which air passes as the piston moves in the cylinder in response to knee flexion, the valve thereby offering variable resistance to the flexion movement.

The control unit preferably performs a preliminary calibration routine in which the adjustment system is operated to set the control unit to a calibration setting at which the unit has a predetermined resistance to flexion and/or extension movements of the knee joint, the calibration routine including operating a monitoring system and the electronic storage device during a walking test to derive an optimum value of the kinetic or kinematic parameter and an associated optimum walking speed value. These values can then be used to define the target relationship.

One particular parameter of locomotion which the applicants have successfully used is a ratio of the flexed state duration and the extended state duration. In particular, this ratio may be the ratio of the time during which, in a walking cycle period, the knee joint may be regarded as being in a flexed state and the time in which, during the cycle period, the knee joint may be regarded as being in an extended state. Transitions between the flexed state and the extended state may be sensed by setting one or more knee angle threshold values.

It will be appreciated that there are related parameters which may be used instead, such as the duration of the flexed state as a proportion of the total cycle period, as well as other threshold-crossing knee angle functions. Indeed, the inverse ratio or proportion may be used.

It is also possible to use, for instance, the maximum knee angle, or a period during which the knee angle exceeds a predetermined value, and so on, as the kinetic or kinematic parameter.

The prosthesis can be self-teaching at all times, but it is preferred that self-teaching only occurs when a self-teaching mode is selected, e.g. by operation of a switch or on detection of a special sequence of movements of the prosthesis. The self-teaching mode may include the calibration routine as an option.

During the self-teaching mode, the control unit may be operated to store electrical signals representative of control unit settings, e.g. damper resistance settings, at different respective walking speeds, which settings are derived from the automatic adjustments made by the adjustment system to bring values of the kinetic or kinematic parameter closer to the target relationship. The monitoring system and the adjustment system are operable in the playback mode respectively to generate real time signals representative of the walking speed and to cause the control unit to be adjusted to the control unit settings in accordance with the generated real time walking speed signals.

Convergence of the parameter to a value defined by the target relationship may be performed by the monitoring system and the adjustment system conjunctively by adjusting the control unit automatically and successively in an iterative manner. Preferably this process is performed for each of a plurality of walking speeds to bring the parameter to an optimum value for each respective walking speed, the resulting control unit settings being stored as a series of values against respective walking speed values, e.g. as a look-up table.

The target relationship preferably comprises a function relating the above-mentioned ratio (the ratio obtained by dividing the flexed state duration by the extended state duration) to a walking cycle period, the function being such that the ratio decreases as the cycle period increases. Such a function, when plotted in a Cartesian coordinate system, is typically in the form of a line, the gradient of which decreases with increasing cycle period. The line may be a curve, or it may be a line having interconnected straight line portions, the line passing through a point representing the above-mentioned optimum parameter value and optimum walking speed value. The gradients of the line are preferably derived from trials with a number of amputees in which samples of the ratio are accumulated and recorded at different walking speeds.

Speeds of locomotion may be defined by a plurality of speed regions or step period regions (one being the reciprocal of the other) stored in the control unit. When the prosthesis is operated to perform a self-teaching routine in each speed region, the parameter is brought closer to a respective value for that speed region as defined by the target relationship. This process may include a comparison of the values of the parameter as represented by the monitoring signals occurring at times of acceleration and/or deceleration with parameter values defined by the target relationship, the adjustment system being caused to adjust the control unit setting, e.g. damping resistance, in response to deviations from the target relationship with exceed a predetermined deviation magnitude or factor.

In a particularly preferred embodiment, the speed regions are, themselves, dynamically and automatically variable in response to the monitoring signals representative of walking speed values. In this way, it is possible to tailor the speed regions to the amputee's preferred range or distribution of walking speeds.

In accordance with another aspect of the invention, a self-teaching lower limb prosthesis for an above-knee amputee includes a dynamically adjustable knee movement control unit arranged to control flexion and/or extension movement of a knee joint of the prosthesis according to speed of walking, settings of the control unit for different walking speed ranges being obtained by comparing values of a sensed kinetic or kinematic parameter of locomotion with target values of the parameter respectively associated with the walking speed ranges, and wherein the boundaries between neighbouring walking speed ranges are dynamically adjustable in response to the distribution of measured walking speed samples within the ranges thereby to adapt the ranges to the walking characteristics of the amputee.

When the control unit is operated in a self-teaching mode and a playback mode, the self-taught walking speed ranges may be used to derive walking speed boundaries which are stored in conjunction with control unit settings so that, in the playback mode, the control unit is adjusted to a setting corresponding to a measured walking speed as determined by the stored relationships, in order that the kinetic or kinematic parameter of locomotion is close to or coincident with the target value associated with the measured walking speed.

The speed of walking may be defined according to a number of non-overlapping speed regions which may be designated "slow", "medium" and "fast", the stored data associating a control unit setting for each range which has been determined by means of the self-teaching process referred to above.

The disclosure which follows refers to a lower limb prosthesis which automatically reacts to measured flexed state/extended state ratio values dynamically to adjust the control unit and which, thereby, affects the flexion and/or the extension of the knee joint. In this way, it is possible to provide a self-teaching adaptive control system for a lower limb prosthesis, the system measuring the variation of one or more kinetic or kinematic parameters associated with the dynamic operation of the limb, and automatically processing the parameter measurements to bring them closer to the target relationship referred to above using an iterative procedure in order to achieve an optimum locomotion characteristic.

The monitoring system may comprise the combination of transducer elements operating as a knee angle sensor and a programmed a microcontroller. The programmed microcontroller and a drive system for a valve in a piston and cylinder device may constitute the adjustment system.

The invention will now be described by way of example with reference to the drawings in which:—

Figures 1, 2:
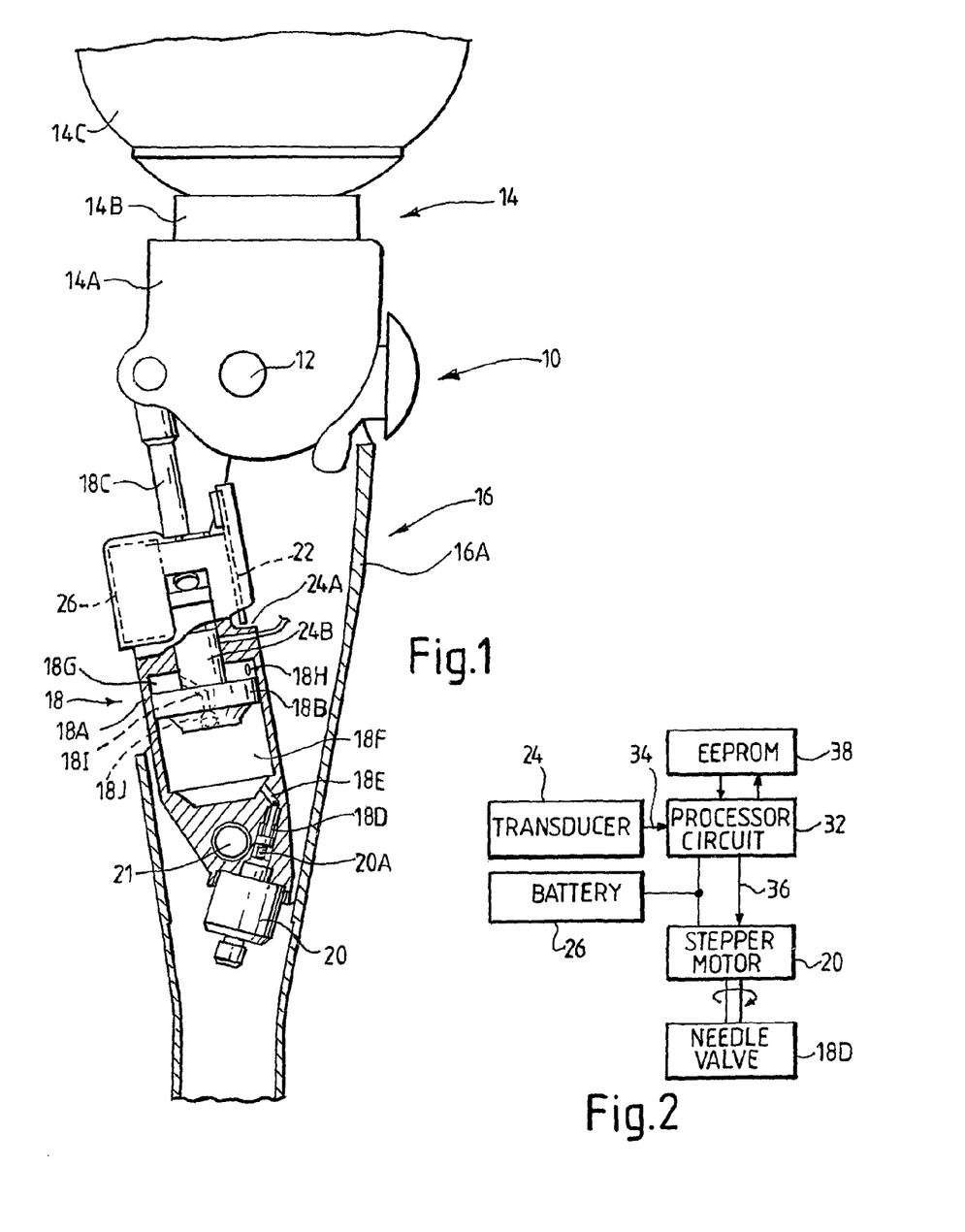
FIG. 1 is a partly sectioned side elevation of part of a lower limb prosthesis incorporating a flexion control device and electronic control elements.
FIG. 2 is a block diagram of a prosthesis control system in accordance with the invention.

A lower limb prosthesis in accordance with the invention is shown in FIG. 1. The prosthesis has a knee joint 10 with a knee pivot 12 connecting a thigh component 14 to a shin component 16. The thigh component comprises a knee chassis 14A, an alignment device 14B, and a stump socket 14C. The shin component 16 has a conventional carbon fibre reinforced plastics shin cradle 16A which houses a piston and cylinder assembly 18 acting as a flexion control device to form part of a control system. The assembly 18 comprises a cylinder 18A which is pivotally coupled to the posterior part of the shin cradle 16A, and a piston 18B having a piston rod 18C which is pivotally coupled to the knee chassis 14A. The piston and cylinder assembly 18 is a pneumatic device, the resistance to flexion of the knee joint being controlled by a needle valve 18D which is adjustable by an electrical stepper motor 20 and an associated screw-threaded shaft 20A connected to the needle member of the needle valve. A d.c. motor may be used as an alternative to a stepper motor. The needle valve 18D lies in a passage 18E in the body of the cylinder 18A, the passage 18E interconnecting the cylinder interior spaces 18F, 18G on opposite sides of the piston 18C and emerging at a port 18H in the wall of the cylinder. Operation of the motor 20 causes the shaft 20A to move axially so that the needle member moves into or out of a passageway forming part of passage 18E.

The passage 18E constitutes a first bypass passage interconnecting the cylinder spaces on opposite sides of the piston 18C. A second bypass passage 18I incorporating a valve such as a one-way valve 18J is formed in the piston 18C so that the needle valve 18D is effective only on one stroke of the piston, in this case the stroke corresponding to increasing flexion of the knee joint 10. The one-way valve 18J may be arranged so as not to close off the second bypass passage 18I completely on the increasing flexion stroke, but rather merely to reduce the orifice area through the piston 18C. Such an arrangement has the effect of the needle valve 18D determining the resistance to motion of the piston 18C in both directions, i.e. for increasing and decreasing flexion, but with the effect of variations in the orifice area of the needle valve 18D being greater in one direction than the other, depending on the direction of operation of the valve 18J.

It is also possible to include a one way valve in the passage communicating with port 18H. The stepper motor 20 and its threaded shaft 20A are mounted in the body of the cylinder 18, preferably adjacent the pivotal coupling 21 of the cylinder 18 to the shin 16.

The stepper motor is driven by a microcomputer which forms part of an electronic circuit assembly 22 and is part of the control system. The microcomputer determines knee flexion and extension movements by means of a magnetic proximity sensor comprising a first part, preferably a transducer 24A, mounted in or associated with the cylinder body 18A, and a second part, preferably a permanent magnet 24B, mounted on or associated with the piston 18B. As an alternative, for instance, transducer 24A may be mounted on a printed circuit board constituting the electronic circuit assembly 22 which is, in turn, associated with cylinder 18. The electronic circuit assembly 22 and the stepper motor 20 are powered by batteries, one of which is shown in FIG. 1 and indicated by the reference 26.

The electronic circuit assembly 22 is shown in more detail in FIG. 2. More particularly, the circuitry comprises a processor circuit 32 which receives transducer signals via input 34 and controls the stepper motor 20 via output 36. A nonvolatile memory in the form of an EEPROM 38 stores walking speed and valve setting data produced by the processor circuit 32, and writes such data to the processor circuit 32 when required.

The processor circuit 32 includes an output driver for driving the stepper motor 20 which in turn moves the needle valve 18D, and it has an input for receiving signals from the flexion sensor 24 comprising transducer 24A and magnet 24B (See FIG. 1).

Signals received from transducer 24A can be interpreted by measuring their width, magnitude, and repetition rate to derive values for the step cycle period (the reciprocal of the walking speed), and the degree of flexion of the knee, herein termed the "knee angle".

Figure 3:
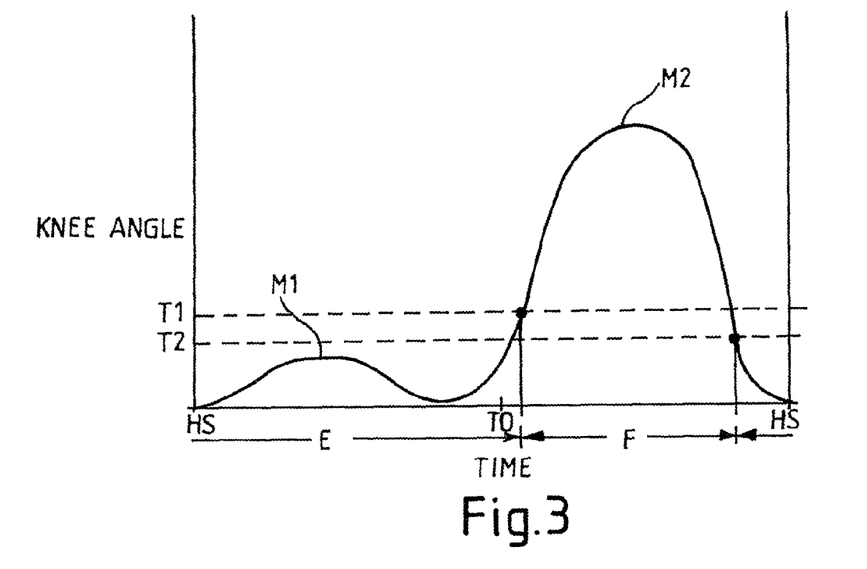
FIG. 3 is a graph showing the variation of knee angle during a walking cycle.

Referring to FIG. 3, during a normal walking cycle the knee angle, i.e. the degree of flexion of the knee joint of the natural limb follows a curve having two knee angle maxima M1, M2. If the beginning of the walking cycle is regarded as being the point at which the heel strikes the ground (the left hand side of the graph of FIG. 3), it will be seen that the knee joint flexes progressively during the stance phase to reach the stance phase knee angle maximum M1 and then extends and flexes again before reaching the toe-off point TO which marks the end of the stance phase and the beginning of the swing phase. During the swing phase, the knee angle continues to increase, reaching a swing phase knee angle maximum M2 approximately in the middle of the swing phase. The knee joint then progressively extends, reaching a minimum knee angle at or just before the next heel strike HS. It will be noted that the swing phase knee angle maximum M2 is much greater than the stance phase knee angle maximum M1.

It has been established that as walking speed varies, the optimal swing resistance of a lower limb prosthesis for an above-knee amputee also varies. It follows that, for a given swing resistance, the amputee has a preferred walking speed. In practice, the amputee, through biomechanical effort, has the dominating influence over the duration of the stance phase whereas the mechanical swing resistance of the prosthetic knee has greater influence over the duration of the swing phase. It follows, that for a given swing resistance setting, the stance phase duration is reduced with increased walking speed, whereas the swing phase duration remains almost constant or exhibits only a slight reduction. This effect has been observed during amputee trials. On this basis, it is predicted that, with a properly adjusted prosthesis, the ratio of the swing phase duration to the stance phase duration increases as walking speed increases.

Referring again to FIG. 3, it can be seen that an approximation to the swing phase to stance phase ratio can be provided by the ratio of a knee flexed state duration to a knee extended state duration. The ratio can be expressed as F/E where F is the flexed state duration as measured by the time interval between the knee angle, firstly, reaching a first knee angle threshold T1 and, secondly, dropping below a second knee angle threshold T2. E is the extended state duration which is the remainder of the cycle period, i.e. the time between crossing the second threshold and crossing the first threshold T1 again.

It is assumed that, for each swing resistance setting, an amputee will have an optimal walking speed and F/E ratio. At a given swing resistance setting, walking speeds above the optimum give rise to a higher F/E ratio and, conversely, slower walking speeds result in a lower F/E ratio.

Consequently, the F/E ratio can be used as a means for determining whether to increase or decrease swing resistance if it deviates from a predetermined optimum value for a given walking speed.

Figure 4:
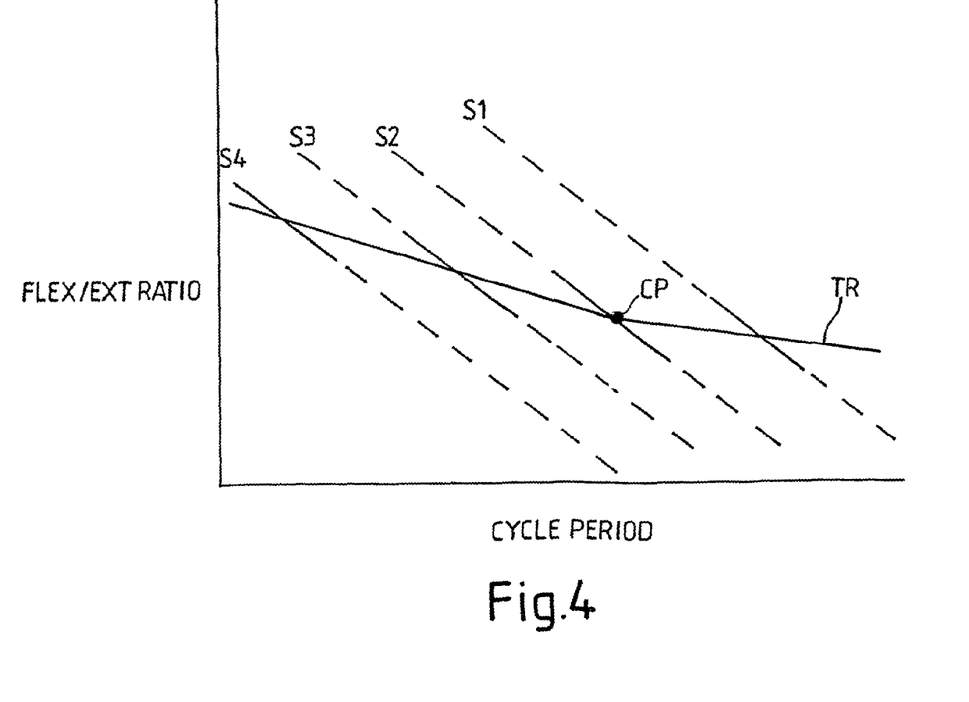
FIG. 4 is a graph plotting the relationship between (a) a flexed state and extended state ratio and (b) step period.

The conclusions reached above are illustrated in the graph of FIG. 4 which relates F/E ratio to the step cycle period (which is the reciprocal of walking speed). Trials conducted with a number of amputees have shown that for a given swing resistance setting, the F/E ratio varies approximately linearly with the cycle period, the relationship having a negative gradient. For a given amputee, at a lower swing resistance, the relationship between the F/E ratio and the cycle period tends to follow a first line S1 with comparatively high F/E ratio values. At a second, higher swing resistance setting, the F/E ratio tends to follow a line of similar gradient but at lower F/E values (see line S2). Similarly, further increases in swing resistance produce further linear relationships with progressively reducing F/E ratio, as shown by lines S3 and S4 in FIG. 4.

The positions of the lines S1 to S4 vary from amputee to amputee, but their essential characteristics, i.e. generally parallel negative-gradient lines spaced in the manner shown tend to apply for all amputees.

A feature which became apparent from the trials is that for each swing resistance setting, an amputee has a preferred walking speed. In each case, this is shown in FIG. 4 by a continuous portion of the line S1, S2, S3, S4. It will be noted that the preferred F/E ratio increases with decreasing step cycle period and with increasing swing resistance. Given that the relationships between F/E ratio, step cycle period, and swing resistance follow a common pattern from amputee to amputee, but have differing values, it is possible to plot the optimum F/E ratio to cycle period characteristic for an amputee, as shown by the line TR in FIG. 3 if an optimum F/E ratio and an optimum walking speed can be determined for a particular swing resistance setting. Thus, for example, if the swing resistance is set to the setting corresponding to one of the lines S2 in FIG. 4 relating F/E ratio to cycle period, and a walking test is performed to establish the preferred F/E ratio and walking speed at that resistance setting, knowledge of the pattern of preferred walking speeds and resulting F/E ratios allows the line TR to be extrapolated from a single calibration point CP on the graph, as shown.

The line TR, therefore, represents a target relationship between the F/E ratio and cycle period for the purposes of adjusting a knee joint control device in a lower limb prosthesis.

Amputee trials have shown that a line of best fit linking points of preferred walking speed and optimum F/E ratio is a curve having a negative gradient with the magnitude of the gradient decreasing with increasing cycle period. To simplify calculation of the target relationship, a dual straight-line characteristic is chosen as a best fit to the curve. It will be seen that, in this example, therefore, the target relationship TR has a first negative gradient portion at cycle period values below the calibration point CP and a second portion for cycle period values higher than the calibration point CP with a different, smaller negative gradient. It will be appreciated that further simplification can be achieved by adopting a continuous straight line target relationship, TR, although it may be expected that less good results may be obtained when used as a the basis for automatic swing resistance setting.

The prior International patent publication WO99/44547 discloses the principle of minimising step-to-step variability of a kinetic or kinematic parameter of locomotion as a means of establishing an optimum setting for a lower limb prosthesis. The same principle is used in the preferred embodiment of the present invention for establishing the calibration point CP, as will be explained below.

Figure 5:
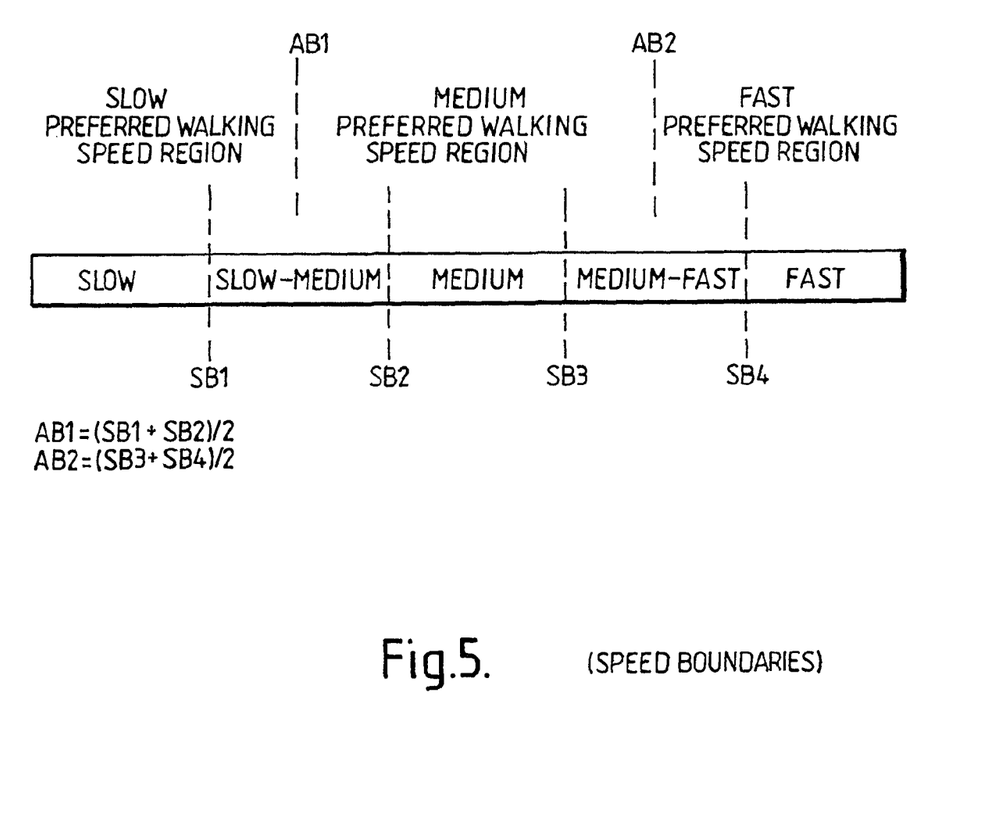
FIG. 5 is a diagram showing the derivation of locomotion speed boundaries for control unit setting.

For the purpose of monitoring or measuring F/E ratio and cycle period, the cycle period is divided into three regions, here referred to as "walking speed" regions, as shown in FIG. 5, the boundaries between the walking speed regions being designated AB1 and AB2. Thus, long cycle periods fall within a "slow" preferred walking speed region lying below boundary AB1, intermediate cycle period values lie in a "medium" preferred walking speed region extending between boundary value AB1 and boundary value AB2, and short cycle period values fall within a "fast" walking speed region above boundary value AB2. These are the walking speed regions which are used in a self-teaching mode of the preferred control system in accordance with the invention when measuring F/E ratio and performing calculations based on the measured values. The choice of three regions is made as a compromise between providing sufficient speed resolution and minimising processing and memory requirements. For the purpose of establishing swing resistance settings, however, a finer speed resolution is used, by defining five secondary walking speed regions divided by secondary boundary values SB1, SB2, SB3, SB4, as shown in FIG. 5. Therefore, for valve setting, secondary slow, slow-medium, medium, medium-fast, and fast speed regions are defined. The relationship between the secondary boundary values and the speed region boundary values AB1, AB2 is defined by the equations:

$$AB1=(SB1+SB2)/2$$

$$AB2=(SB3+SB4)/2$$

Operation of the processor circuit 32 in accordance with an internally stored program will now be described. This program provides a self-teaching facility for determining control device valve settings automatically without intervention by a prosthetist. The programmed processor 32 and the flexion sensor 24 operate in combination as a monitoring system for generating monitoring signals representative of step cycle period values (and hence walking speed values) and of values of the F/E ratio obtained by measuring the times between threshold-crossing events as described above with reference to FIG. 3. The programmed processor circuit 32 operates in conjunction with the stepper motor 20 as an adjustment system which adjusts the valve, thereby to alter swing resistance according to setting stored in the processor circuit 32 or the EEPROM 38.

Figure 6:
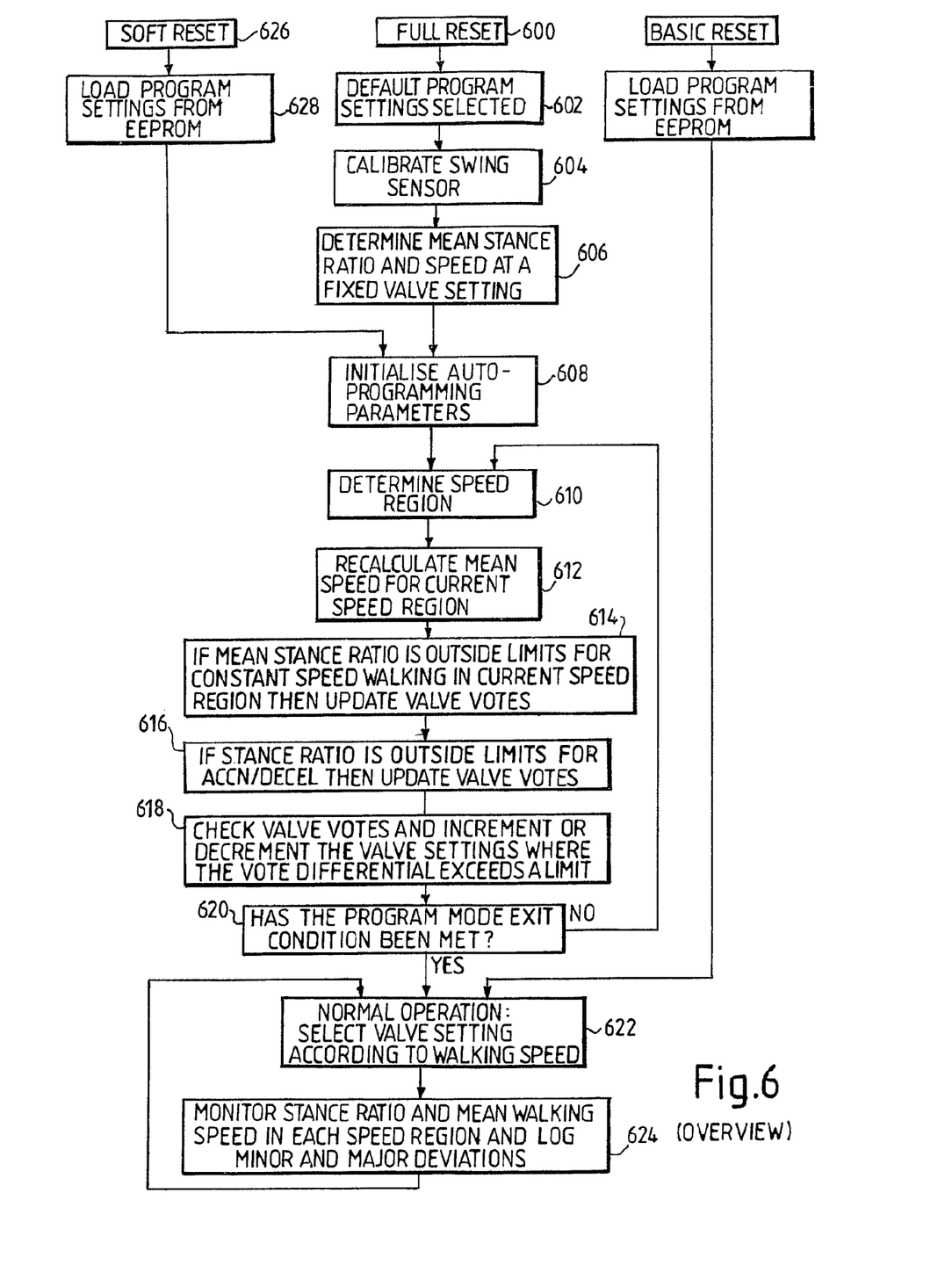
FIG. 6 is a program overview flowchart.

An overview of the program operated by the processor circuit 32 is provided by the flowchart of FIG. 6. Referring to FIG. 6, part or all of the program may be used, depending on whether a full reset of stored valve settings is required, including re-calibration of the system, or self-teaching without recalibration, or normal operation, i.e. using valve settings from a previous self-teaching session.

Full operation of the program starts with a full reset command 600 causing the selection of factory-set valve and walks speed settings in step 602, followed by calibration of the flexion sensor or swing sensor 24 in step 604.

Next, the amputee walking on the prosthesis with the control unit valve driven to a predetermined and fixed calibration setting in order to establish calibration values of the F/E ratio ("stance ratio" in FIG. 6) and walking speed (cycle period), i.e. to establish the calibration point CP shown in FIG. 4. This calibration step appears as step 606 in FIG. 6. Calibration step 606 will be described in more detail hereinafter.

When the control system has established the calibration point, it automatically enters a self-teach mode which begins with initialisation of self-teach programming parameters (step 608) and then performs a series of steps 610, 612, 614, 616, 618 in which walking speed regions stored by the system are tailored to the amputee's requirements automatically and valve settings are established in respect of the walking speed regions by sensing the deviation of measured F/E ratio values from target F/E ratio values defined by the target relationship described above with reference to FIG. 4. Steps 610, 612, 614, 616 and 618 are performed while the amputee is walking. For the full self-teaching operation to be completed, the amputee should walk over the full range of walking speed values normally used.

In step 610, walking speed is measured to determine in which of the walking speed regions defined by the boundaries AB1 and AB2 in FIG. 5 the current walking speed falls. A series of consecutive walking steps having cycle periods corresponding to that region are used to derive a mean speed which is stored for subsequent resetting of the boundary values AB1, AB2 if required, as will be described below. When consecutive steps having cycle periods falling within one of the speed regions (here termed the "current" speed region) are detected, the F/E ratio for each is measured and a mean F/E ratio value calculated, the mean value then being compared with the target value for that speed region. If the comparison indicates a deviation having a magnitude greater than a first limit value, a "vote" signal is generated and stored in a register. These operations are performed for constant speed walking in step 614 and for acceleration and deceleration periods in step 616.

In step 618, the accumulated vote signals representing "votes" for adjusting the valve in one direction or the other are evaluated and the respective valve setting is incremented or decremented when a resultant vote exceeds a predetermined limit.

The amputee can choose to exit the self-teaching mode at this point by, in the preferred embodiment, holding the knee joint in a fully flexed condition for a predetermined period (step 620). If the exit condition has not been met, walking speed region and valve setting updating is repeated, preferably until all three walking speed regions have been updated.

In this way, the F/E ratio is used by self-teaching algorithms in the program in two ways to influence swing resistance adjustment:
1. By comparing the mean F/E ratio with the calibrated target F/E ratios when maintaining a plurality of consecutive steps within a given speed region; and
2. By comparing the F/E ratio for the second of a sequence of three walking steps, wherein the three steps constitute an acceleration episode or a deceleration episode across a speed region boundary (AB1 or AB2 in FIG. 5), with the calibrated target F/E ratios.

In either case, a mean measured F/E ratio above the target ratio for the corresponding walking speed causes generation of a "vote" for an increase of the swing resistance for that region. Conversely, a mean measured F/E ratio lower than the target ratio causes generation of a "vote" for a decrease in the swing resistance for that speed region. As the votes are accumulated over a period, votes for a swing resistance increase cancel out votes for a swing resistance decrease and at the end of the accumulation period, the net sum of votes is evaluated. When the next sum for any given speed region exceeds a predetermined threshold, the swing resistance corresponding to that voting region is increased or decreased depending on the bias of the votes.

The self-teaching mode routine will be described in more detail hereinafter.

Upon exiting the self-teaching mode (step 620) the program enters a playback mode ("normal operation") in which the updated valve settings established in the self-teaching mode are used to set the valve according to walking speed (step 622) as the amputee walks. In this embodiment of the invention, the playback mode also includes a monitoring step 624 in which the F/E ratio and the mean cycle period are monitored in each speed region and minor or major deviations are logged.

In situations in which it is not necessary to perform the calibration routine, the program may be started from a soft reset command 626 wherein following the loading of program settings from the EEPROM (step 628), the program enters the self-teaching mode downstream of the calibration step.

Alternatively, if the control system has been deactivated and normal operation is required, based on existing valve settings and walking speed settings, the program can be entered through a basic reset command 630 which, after loading program settings from the EEPROM (step 632), the program is entered at the normal operation playback mode (step 622).

Figure 7:
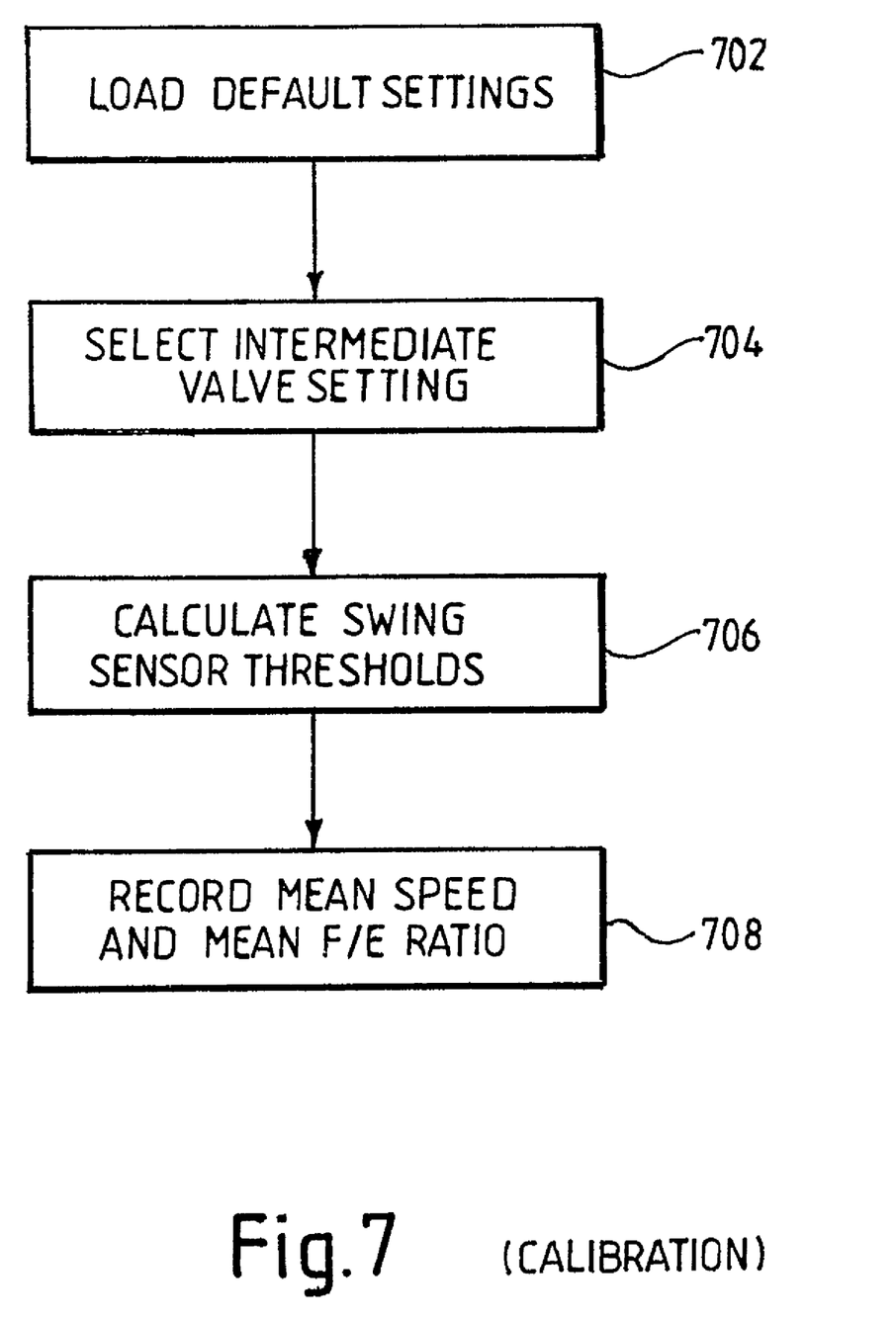
FIG. 7 is a flowchart for a calibration routine.

Now, referring to FIG. 7, the calibration routine is described. This routine begins with the loading of factory-set default settings in step 702 and the selection of a fixed, calibration, valve setting which is well above and well below the expected lowest and highest resistance settings to be used by the amputee (step 704). Then the swing sensor is calibrated by selecting knee angle thresholds which, according to the sensor outputs, are in the lower part of the knee angle range traversed during the swing phase, but above the maximum knee angle encountered during the stance phase, as measured during a series of walking steps, preferably four steps. These knee angle thresholds appear in FIG. 3 as knee angle values T1 and T2. These threshold values are used to detect the start and finish of the flexed state of the knee joint. Entry into the flexed state is detected using a higher knee angle threshold than that used for exit detection in order to avoid control system instability. (It should be noted that "knee angle" in this context means the relative angle between the axes of the upper and lower limb components joined by the knee joint, which angle is zero at full extension and increases as the knee joint is flexed.)

Having calibrated the swing sensor by calculating the swing sensor thresholds in step 706, a speed and F/E ratio calibration operation 708 is performed in which the amputee walks at a speed which to him or her is the preferred speed for the fixed valve setting. The system measures the step-to-step variability of the cycle period and the F/E ratio over a number of steps and, when several consecutive steps have been completed with the measured speed and measured F/E ratio remaining substantially constant within predetermined limits, the mean cycle period and the mean F/E ratio value for those steps are calculated and stored as the calibration values representing the calibration point CP described above with reference to FIG. 4. These values are used during the self-teaching routine to calculate the target relationship TR between F/E ratio and cycle period described above with reference to FIG. 4.

Figure 8:
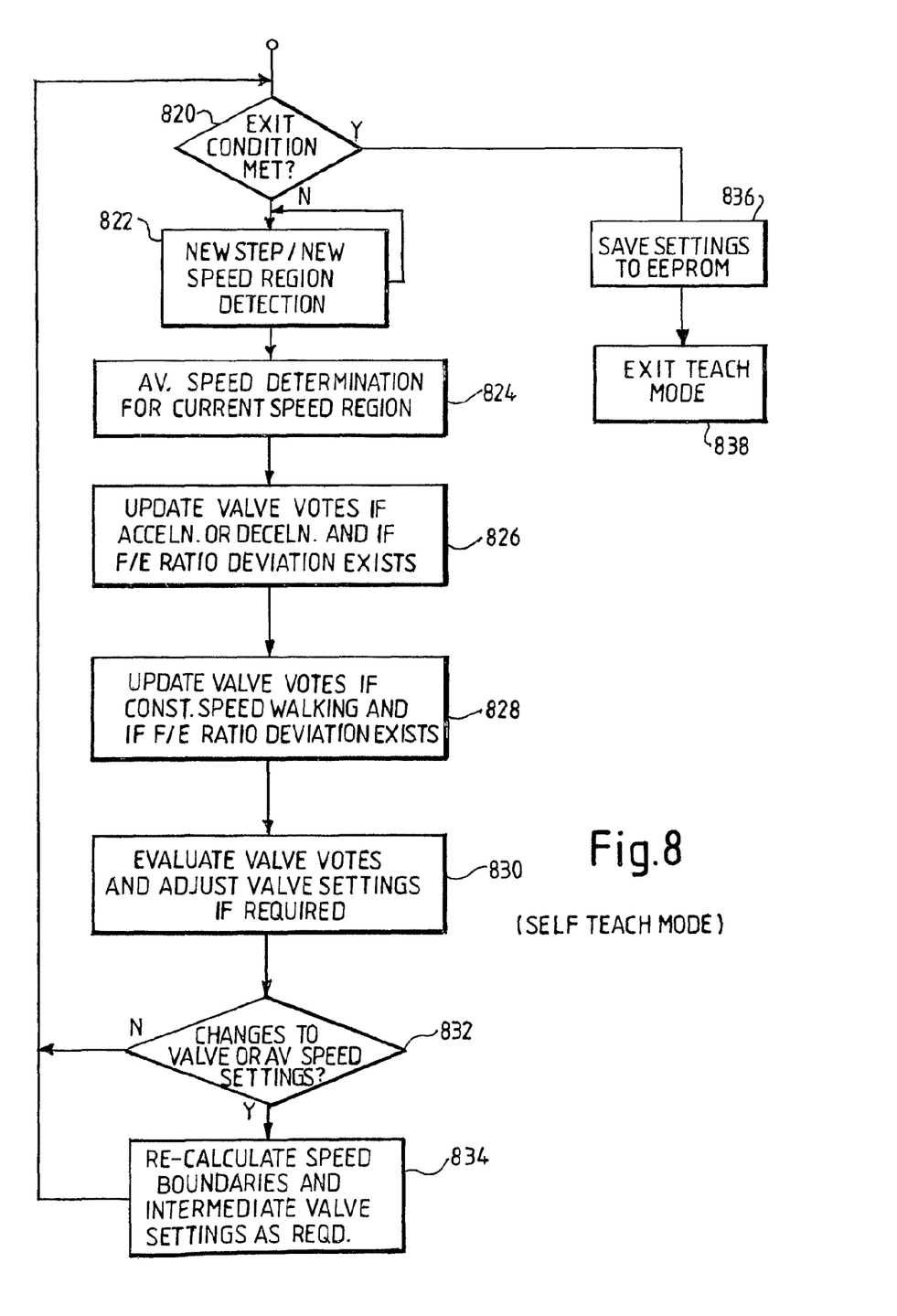
FIG. 8 is a flowchart for a self-teaching routine.

The self-teaching mode will now be described in more detail with reference to FIG. 8.

As mentioned above, the self-teaching mode has an exit condition which is detected in step 820. If this exit condition is not met, the program proceeds to step 822 in which it loops back until a new step is detected. If the cycle period of the new step indicates that the walking speed has moved to a new speed region, a contiguous step count is cleared. If not, the contiguous step count is maintained at this point.

Next, an average speed value is determined by measuring the cycle period over four consecutive steps in the current speed region and dividing the sum by four. The average speed value is stored. (In practice, the average speed value used for average speed determination is the average of a number of these four-step averages.) These operations take place in step 824. Generation of voting signals during acceleration and deceleration episodes in step 826 and during constant speed periods in step 828 takes place concurrently with the average speed determination of step 824. These operations are described in more detail below. Evaluation of the "votes" (see step 830) occurs in respect of each walking step on the basis of votes accumulated over a number of steps occurring in the same speed region as the current speed region. Votes for an increase in swing resistance may be regarded as positive votes and votes for a decrease in swing resistance as a negative vote.

Summing accumulated votes produces a resultant value which, if it exceeds a predetermined amount (in this case the amount has a magnitude of 2), causes an adjustment of the valve setting by a predetermined increment.

If the votes do not reach two votes in one direction or the other, no adjustment of the valve occurs. A valve setting adjustment or a change in the average speed as determined in step 824, as detected in step 832, causes recalculation of the speed boundaries as described above with reference to FIG. 5 (see step 834). At the same time, if a new valve setting has been established for any of the slow, medium and fast walking speed regions defined by the boundaries AB1 and AB2 shown in FIG. 5, new interpolated valve settings for the secondary speed regions are computed.

Whether or not changes to the valve or average speed settings have occurred, the steps of the self-teach mode are repeated until the exit condition is met in step 820. When the exit condition is satisfied, the new speed boundaries and valve settings are saved in the EEPROM and the teach mode is exited (steps 836, 838).

The generation of voting signals for adjusting the valve setting is performed both in respect of acceleration/deceleration episodes and constant speed periods. However, in alternative embodiments, it is possible to base valve settings on either one of these.

Figure 9:
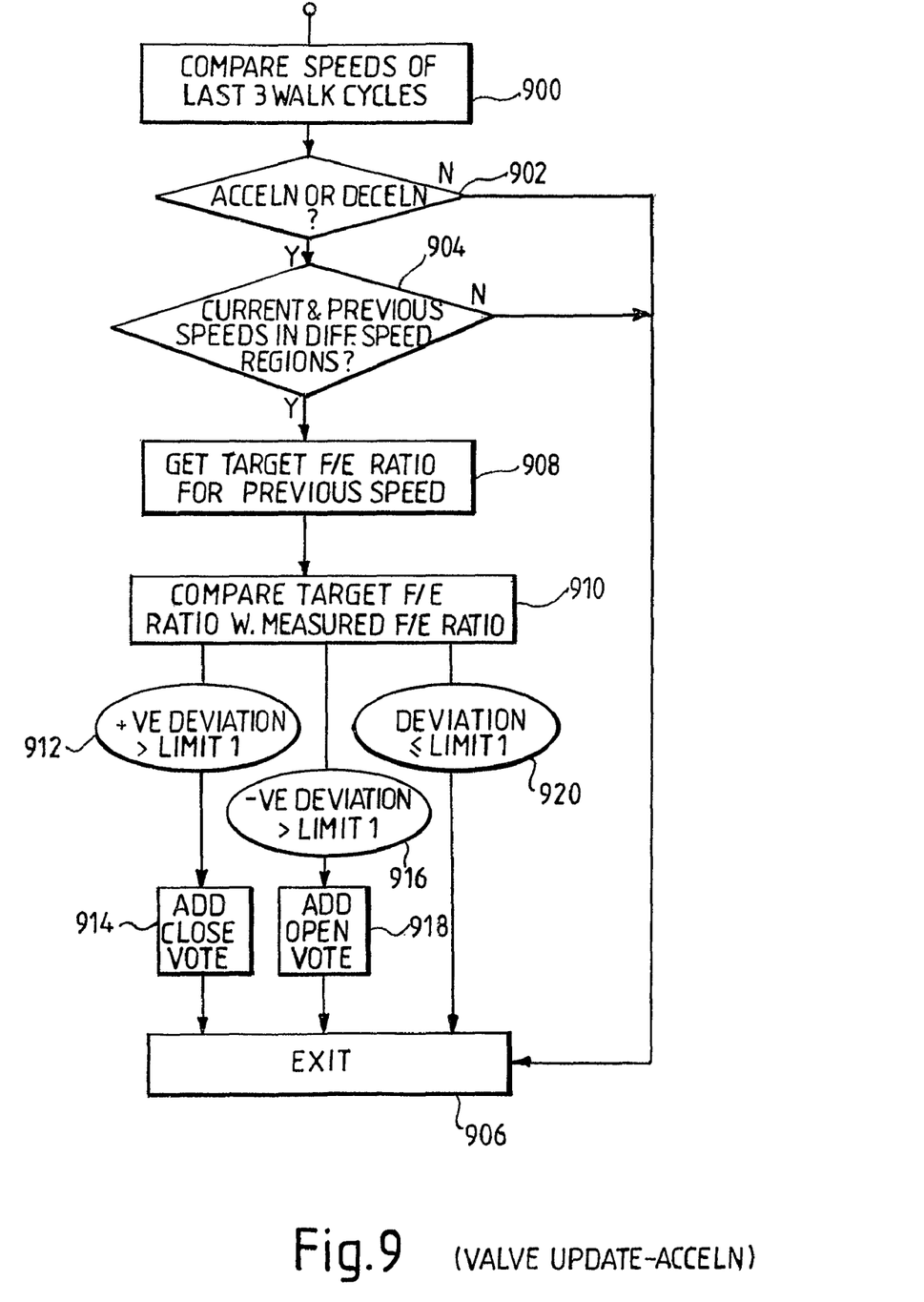
FIG. 9 is a flowchart for a first control unit setting routine.

Referring to FIG. 9, the generation of voting signals for acceleration and deceleration episodes starts by detecting acceleration or deceleration using a comparison of the cycle periods of three consecutive walk step cycles, as indicated in FIG. 9 by step 900. If acceleration or deceleration is detected (step 902), the system next determines whether the acceleration or deceleration has resulted in one of the speed boundaries AB1, AB2 (see FIG. 5) having been crossed (step 904). If neither of these conditions has been met, the voting signal generation routine for acceleration and deceleration is exited via exit step 906.

If, on the other hand, there has been acceleration or deceleration across a speed boundary, the target F/E ratio for the starting speed region (i.e. the speed region in which the walking speed fell before the speed boundary crossing occurred) is calculated based upon the target relationship defined by the calibration point CP set in the last calibration operation. The derivation of the target relationship is described above with reference to FIG. 4. Therefore, in step 908, a target F/E ratio for the pre-existing speed region is obtained. This F/E ratio value is compared with the current measured F/E ratio value for the pre-existing speed region (step 910). If the result of this comparison indicates a positive F/E ratio deviation of the measured value relative to the target value by an amount greater than a first limit value, then a "valve close" vote is generated (steps 912, 914). Conversely, if the deviation is negative and of an amount greater than the first limit, a "valve open" vote is generated (steps 916, 918). If there is no deviation or the deviation is less than or equal to the limit value, no vote is registered (step 920). In the exit step 906, any "votes" are registered. Each time this routine is performed, the votes are registered so that, over several steps, votes are accumulated as described above.

Figure 10:
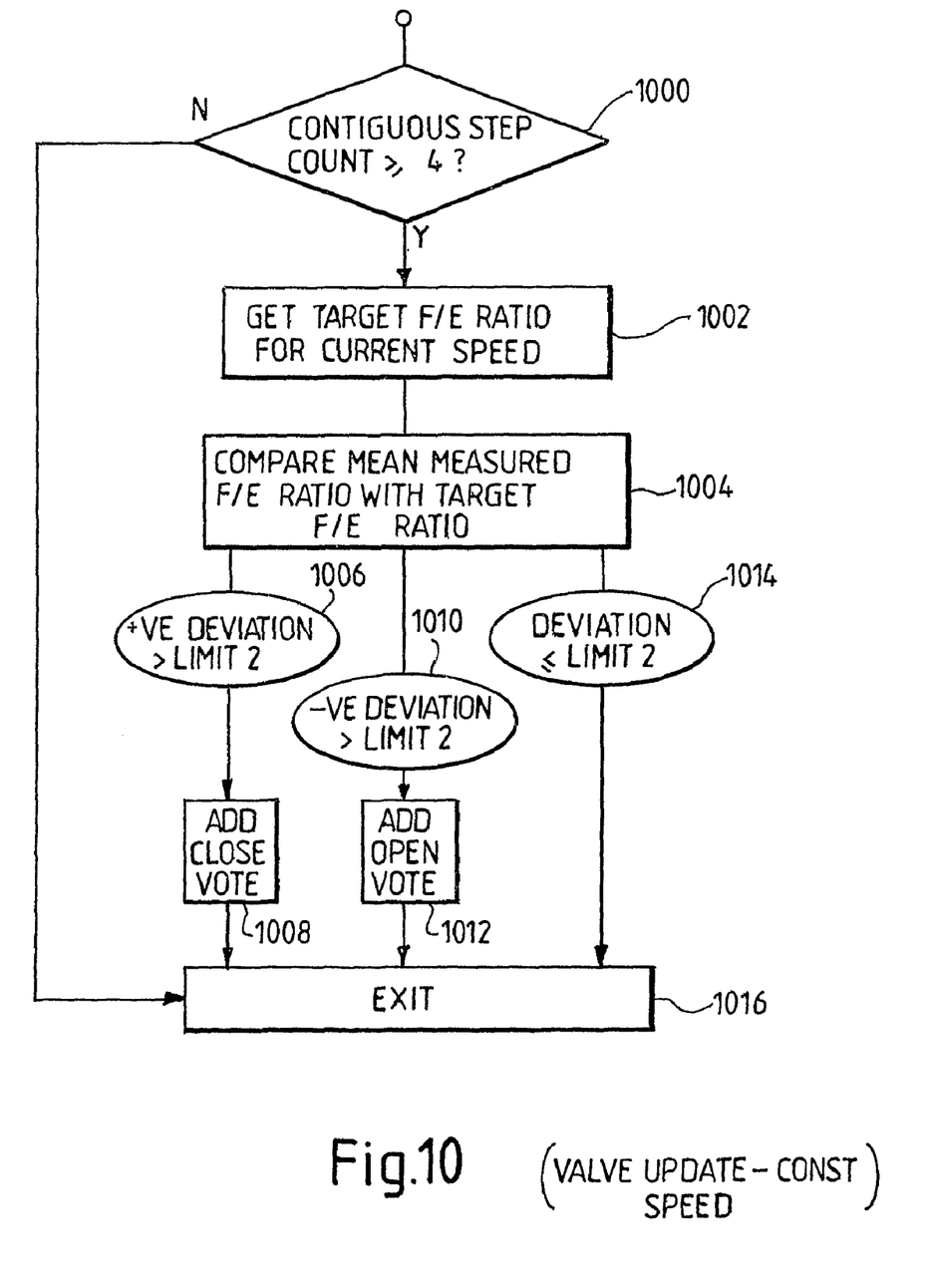
FIG. 10 is a flowchart for a second control unit setting routine.

Referring to FIG. 10, a similar process is performed for accumulating valve adjustment votes during constant speed periods. Thus, in step 1000, the system determines whether there have been four contiguous walking cycle steps. A positive result causes the system to calculate the target F/E ratio for the current speed region (slow, medium, or fast as described above with reference to FIG. 5) (see step 1002). Next, the F/E ratio values measured for the last four steps are averaged to obtain a mean measured F/E ratio value which is then compared with the target F/E ratio value for the current speed region (step 1004).

In the same manner as described above with reference to FIG. 9, deviations of the mean measured F.E ratio with respect to the target F/E ratio give rise to a "close vote" or an "open vote", or no vote. In this case, a different limit is used for discriminating the deviation values, this limit being lower than the limit used for the acceleration/deceleration episodes. The steps for determining the generation of votes appear in FIG. 10 as steps 1006, 1008, 1010, 1012, and 1014.

The accumulated votes are periodically totaled in the manner described above to allow valve adjustments as required, as described above with reference to FIG. 8.

The invention claimed is:

1. A self-teaching lower limb prosthesis for an above-knee amputee, the prosthesis comprising:
    an upper limb portion and a lower limb portion connected to each other by a knee joint that allows flexion and extension of the limb portions relative to each other; and
    a dynamically adjustable knee movement control unit arranged to control flexion and/or extension movements of the knee joint of the prosthesis so as to adjust the rate at which the knee joint swings, wherein the control unit comprises:
        an electronic storage device storing a target relationship between walking speed and a parameter that is a ratio of (i) a flexed state duration of an amputee's gait during use of the prosthesis to (ii) one of an extended state duration and a total cycle period of the amputee's gait during use of the prosthesis, the relationship defining a plurality of values of the parameter associated with different respective walking speeds,
        a monitoring system comprising a sensor arranged to sense flexion and extension movements of the knee joint and a processor that receives signals from the sensor and processes the signals to generate monitoring signals representative of walking speed values and values of the parameter occurring during use of the prosthesis at different walking speeds, and
        an adjustment system arranged to adjust the control unit automatically in response to said monitoring signals indicating deviation of the parameter from the target relationship, such that:
        when the parameter is below the target relationship at a given walking speed the adjustment system adjusts the control unit to reduce the rate at which the knee joint swings; and
        when the parameter is above the target relationship at a given walking speed the adjustment system adjusts the control unit to increase the rate at which the knee joint swings.

2. A prosthesis according to claim 1, wherein the monitoring and adjustment systems are respectively arranged to generate the monitoring signals over a plurality of walking step cycles and to calculate a parameter deviation value based on said signals for said plurality of step periods, the control unit adjustment being made in response to the parameter deviation value.

3. A prosthesis according to claim 1, wherein the adjustment system is arranged to perform the control unit adjustments in increments so as to bring the parameter successively closer to a value defined by the target relationship on the basis of monitoring signals obtained for a plurality of walking step cycles occurring within a single walking speed region.

4. A prosthesis according to claim 1, wherein the control unit is operable to perform a calibration routine in which the adjustment system is operated to set the control unit to a calibration setting at which the unit has a predetermined resistance to flexion and/or extension movements of the knee joint, the calibration routine including operating the monitoring system and electronic storage device during a walking test to derive an optimum value of said parameter and an associated optimum walking speed value, which values are used to define said target relationship.

5. A prosthesis according to claim 1, wherein the control unit is operable in a self-teaching mode and a playback mode, and is arranged to store during the self-teaching mode electrical signals representative of control unit settings at different respective walking speeds, which settings are derived from the automatic adjustments made by the adjustment system to bring values of said parameter closer to the target relationship, and wherein the monitoring system and adjustment system are operable in the playback mode respectively to generate real time signals representative of the walking speed and to cause the control unit to be adjusted to said control unit settings in accordance with the generated real time walking speed signals.

6. A prosthesis according to claim 1, wherein the monitoring system and the adjustment system are arranged to adjust the control unit automatically and successively in an iterative manner for each of a plurality of walking speeds to bring the parameter closer to the value defined by the target relationship for the respective walking speed.

7. A prosthesis according to claim 1, wherein the target relationship comprises a function relating said ratio to walking cycle period, the function being such that the ratio decreases as the cycle period increases.

8. A prosthesis according to claim 7, wherein the function, when plotted in a cartesian coordinate system, is in the form of a line the gradient of which decreases with increasing cycle period.

9. A prosthesis according to claim 1, wherein the control unit is operable to define a plurality of walking speed regions and to perform a self-teaching routine in which, in respect of each walking speed region, the parameter is brought closer to a respective value for that speed region as defined by the target relationship.

10. A prosthesis according to claim 9, wherein the control unit is arranged to compare the values of the parameter represented by the monitoring signals occurring at times of acceleration and/or deceleration with values defined by the target relationship, the adjustment system being caused to adjust the control unit setting in response to deviations from the target relationship of a magnitude greater than a predetermined amount.

11. A prosthesis according to claim 9, wherein the walking speed regions are dynamically and automatically variable in response to said monitoring signals representative of walking speed values.

12. A self-teaching lower limb prosthesis for an above-knee amputee, wherein the prosthesis includes a knee joint and a dynamically adjustable knee movement control unit arranged to control flexion and/or extension movement of the knee joint of the prosthesis according to speed of walking so as to adjust the rate at which the knee joint swings, the control unit including an electronic storage device storing a target relationship between walking speed and a parameter of locomotion that is a ratio of (i) a flexed state duration of an amputee's gait during use of the prosthesis to (ii) one of an extended state duration and a total cycle period of the amputee's gait during use of the prosthesis, the relationship defining a plurality of values of the parameter of locomotion associated with different respective walking speed ranges, settings of the control unit for the different walking speed ranges being obtained by comparing sensed values of said parameter of locomotion with target values of the parameter respectively associated with the walking speed ranges such that when the sensed value of the parameter is below the target value at a given walking speed the adjustment system adjusts the control unit to reduce the rate at which the knee joint swings, and when the sensed value of the parameter is above the target value at a given walking speed the adjustment system adjusts the control unit to increase the rate at which the knee joint swings, and wherein the control unit is operable to dynamically adjust boundaries between neighbouring walking speed ranges in response to a distribution of measured walking speed samples within the ranges thereby to adapt the ranges to the walking characteristics of the amputee.

* * * * *

UNITED STATES PATENT AND TRADEMARK OFFICE
CERTIFICATE OF CORRECTION

| | | |
|---|---|---|
| PATENT NO. | : 8,403,997 B2 | Page 1 of 1 |
| APPLICATION NO. | : 12/282541 | |
| DATED | : March 26, 2013 | |
| INVENTOR(S) | : Sykes et al. | |

It is certified that error appears in the above-identified patent and that said Letters Patent is hereby corrected as shown below:

Title page,
Insert the following:
-- Related U.S. Application Data
(60) Provisional application No. 60/807,505, filed on Jul. 17, 2006. --.

Signed and Sealed this
Thirtieth Day of July, 2013

Teresa Stanek Rea
*Acting Director of the United States Patent and Trademark Office*